United States Patent [19]

McCune et al.

[11] E Re. 29,182

[45] Reissued Apr. 12, 1977

[54] ORAL COMPOSITION FOR CALCULUS RETARDATION

[75] Inventors: Homer W. McCune, Wyoming; Nathaniel B. Tucker, Glendale, both of Ohio

[73] Assignee: The Procter & Gamble Company, Cincinnati, Ohio

[22] Filed: June 14, 1976

[21] Appl. No.: 696,019

Related U.S. Patent Documents

Reissue of:

[64] Patent No.: 3,488,419
Issued: Jan. 6, 1970
Appl. No.: 731,312
Filed: May 22, 1968

U.S. Applications:

[63] Continuation-in-part of Ser. No. 693,713, Dec. 27, 1967, abandoned, which is a continuation-in-part of Ser. No. 668,702, Sept. 18, 1967, abandoned, which is a continuation-in-part of Ser. No. 512,548, Dec. 8, 1965, abandoned.

[52] U.S. Cl. ..... 424/49; 424/54; 424/57

[51] Int. Cl.[2] ..... A61K 7/16

[58] Field of Search ..... 424/49–58

[56] References Cited

UNITED STATES PATENTS

| | | | |
|---|---|---|---|
| 2,191,199 | 2/1940 | Hall | 424/57 |
| 3,159,581 | 12/1964 | Diehl | 260/502.4 |
| 3,213,030 | 10/1965 | Diehl | 252/152 |
| 3,214,454 | 10/1965 | Blaser et al. | 260/502.4 |
| 3,297,578 | 1/1967 | Crutchfield et al. | 260/502.4 |
| 3,299,123 | 1/1967 | Fitch et al. | 260/502.4 |
| 3,303,139 | 2/1967 | Blaser et al. | 252/180 |
| 3,400,148 | 9/1968 | Quimby | 260/502.4 |
| 3,400,176 | 9/1968 | Quimby | 260/502.4 |
| 3,671,644 | 6/1972 | Irani et al. | 424/346 |

OTHER PUBLICATIONS

Dental Abstracts, vol. 12, No. 9, pp. 539–544, Sept. 1967.

Draus et al.: Dental Progress, vol. 3, No. 2, pp. 79–81 Jan. 1963.

Grossman: J. Oral Surgery, Oral Medicine, and Oral Pathology, vol. 7, pp. 484–487, May 1954.

*Primary Examiner*—Shep K. Rose

*Attorney, Agent, or Firm*—George W. Allen; Richard C. Witte; J. D. Schaeffer

[57] ABSTRACT

Oral compositions, such as toothpaste, mouthwash, and the like, containing certain polyphosphonic acids and their salts which retard dental calculus formation without damaging tooth structure.

21 Claims, No Drawings

ORAL COMPOSITION FOR CALCULUS RETARDATION

Matter enclosed in heavy brackets [ ] appears in the original patent but forms no part of this reissue specification; matter printed in italics indicates the additions made by reissue.

CROSS-REFERENCE TO RELATED APPLICATIONS

This application is a continuation-in-part of the copending application of Homer W. McCune and Nathaniel B. Tucker, Ser. No. 693,713, filed Dec. 27, 1967, which is a continuation-in-part of copending application Ser. No. 668,702, filed Sept. 18, 1967, which in turn is a continuation-in-part of copending application Ser. No. 512,548, filed Dec. 8, 1965, all now abandoned.

BACKGROUND OF THE INVENTION

The field of this invention is "oral compositions" which term is used herein to designate products which in the ordinary course of usage are retained in the oral cavity for a time sufficient to contact substantially all of the dental surfaces, but are not intentionally ingested. Such products include, for example, dentifrices, mouthwashes, prophylaxis pastes and topical solutions.

Dental calculus, or tartar as it is sometimes called, is a deposit which forms on the surfaces of the teeth at the gingival margin. Supraginival calculus appears principally in the areas near the orifices of the salivary ducts; e.g., on the lingual surfaces of the lower anterior teeth and on the buccal surfaces of the upper first and second molars, and on the distal surfaces of the posterior molars.

Mature calculus consists of an inorganic portion which is largely calcium phosphate arranged in a hydroxylapatite crystal lattice structure similar to bone, enamel and dentine. An organic portion is also present and consists of desquamated epithelial cells, leukocytes, salivary sediment, food debris and various types of microorganisms.

As the mature calculus develops, it becomes visibly white or yellowish in color unless stained or discolored by some extraneous agency. In addition to being unsightly and undesirable from an aesthetic standpoint, the mature calculus deposits are constant sources of irritation of the gingiva and thereby are a contributing factor to gingivitis and other diseases of the supporting structures of the teeth, the irritation decreasing the resistance of tissues to endogeneous and exogenous organisms.

A wide variety of chemical and biological agents have been suggested in the art to retard calculus formation or to remove calculus after it is formed. Mechanical removal of this material periodically by the dentist is, of course, routine dental office procedure.

The chemical approach to calculus inhibition generally involves chelation of calcium ion which prevents the calculus from forming and/or breaks down mature calculus by removing calcium. A number of chelating agents have been employed for this purpose. See, for example, British Patent 490,384, granted Feb. 15, 1937, which discloses oral compositions containing ethylenediamine-tetraacetic acid, nitrilotriacetic acid and related compounds as anticalculus agents; German Auslegeschrift 1,149,138, published May 22, 1963, which discloses certain water-soluble diglycolates as anticalculus agents; and U.S. Pat. No. 1,516,206 which discloses oral compositions containing various sugar lactones for this purpose.

Although certain of the art-disclosed chelators are purportedly safe for use on dental enamel, the chemical similarity of calculus to the tooth structure limits the usefulness of the chelation approach since the more effective chelators can seriously damage the tooth structure by decalcification. Thus, the development of oral compositions which effectively retard calculus by calcium chelation has been impeded by safety considerations.

SUMMARY OF THE INVENTION

It has now been discovered that certain polyphosphonic acids and salts thereof (referred to collectively hereinafter as "polyphosphonates") possess the surprising capacity to retard the development of dental calculus without removing calcium from dental enamel or otherwise damaging the tooth structure when employed in oral compositions maintained within defined pH limits.

Operable polyphosphonates for use in the compositions of this invention are characterized in that their molecular structure contains at least two geminal or three vicinal phosphono groups. Although these compounds may possess only nominal calcium sequestering capacities in the pH range characteristic of oral compositions, they effectively retard calculus formation by a mechanism that is believed to involve the inhibition of hydroxylapatite crystal growth as will be discussed more fully hereinafter.

Unlike inorganic polyphosphates such as pyrophosphates, the polyphosphonates employed in the compositions of this invention resist hydrolysis in aqueous products and therefore remain in an active form throughout the normal shelf-life of such products.

It is therefore an object of this invention to provide novel oral compositions which retard the formation of calculus without otherwise affecting the tooth structure.

It is another object of this invention to provide an improved method for retarding the development of dental calculus.

Other objects will become apparent from the following detailed description.

DETAILED DESCRIPTION OF THE INVENTION

This invention is an oral composition effective in inhibiting the formation of dental calculus without adversely affecting the tooth structure comprising from about .01% to about 10% by weight of a polyphosphonate selected from the group consisting of those of the formulae:

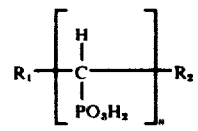

(1)

or

-continued

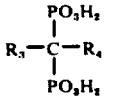

(II)

wherein $R_1$ and $R_2$ are hydrogen or $CH_2OH$; n is an integer of from 3 to 10; $R_3$ is hydrogen, alkyl containing from 1 to about 20 carbon atoms, alkenyl containing from 2 to about 20 carbon atoms, aryl (e.g., phenyl and naphthyl), phenylethenyl, benzyl, halogen (e.g., chlorine, bromine, and fluorine), amino, substituted amino (e.g., dimethylamino, diethylamino, N-hydroxy-N-ethylamino, acetylamino), $—CH_2COOH$, $—CH_2PO_3H_2$, $—CH(PO_3H_2)(OH)$ or $—CH_2CH(PO_3H_2)_2$; $R_4$ is hydrogen, lower alkyl (e.g., methyl, ethyl, propyl, and butyl), amino, benzyl, halogen (e.g., chlorine, bromine and fluorine), hydroxyl, $—CH_2COOH$, $—CH_2PO_3H_2$, or $—CH_2CH_2PO_3H_2$; or a pharmaceutically acceptable salt thereof such as alkali metal (e.g., sodium and potassium), alkaline earth metal (e.g., calcium and magnesium), and ammonium or low molecular weight substituted ammonium (e.g., mono-, di-, and triethanolammonium) salts, and a carrier suitable for use in the oral cavity, the pH of the composition being within the range from about 5.0 to about 11.0.

Operable polyphosphonates of the above Formula I include propane-1,2,3-triphosphonic acid;
butane-1,2,3,4-tetraphosphonic acid;
hexane-1,2,3,4,5,6-hexaphosphonic acid;
hexane-1-hydroxy-2,3,4,5,6-pentaphosphonic acid;
hexane-1,6-dihydroxy-2,3,4,5-tetraphosphonic acid;
pentane-1,2,3,4,5-pentaphosphonic acid;
heptane-1,2,3,4,5,6,7-heptaphosphonic acid;
octane-1,2,3,4,5,6,7,8-octaphosphonic acid;
nonane-1,2,3,4,5,6,7,8,9-nonaphosphonic acid;
decane-1,2,3,4,5,6,7,8,9,10-decaphosphonic acid;

and the pharmaceutically acceptable salts of these acids, e.g., sodium, potassium, calcium, magnesium, ammonium, triethanolammonium, diethanolammonium, and monoethanolammonium salts.

Among the operable polyphosphonates encompassed by the above Formula II are ethane-1-hydroxy-1,1-diphosphonic acid;
methanediphosphonic acid;
methanehydroxydiphosphonic acid;
ethane-1,1,2-triphosphonic acid;
propane-1,1,3,3-tetraphosphonic acid;
ethane-2-phenyl-1,1-diphosphonic acid;
ethane-2-naphthyl-1,1-diphosphonic acid;
methanephenyldiphosphonic acid;
ethane-1-amino-1,1-diphosphonic acid;
methanedichlorodiphosphonic acid;
nonane-5,5-diphosphonic acid;
n-pentane-1,1-diphosphonic acid;
methanedifluorodiphosphonic acid;
methanedibromodiphosphonic acid;
propane-2,2-diphosphonic acid;
ethane-2-carboxy-1,
1-diphosphonic acid;
propane-1-hydroxy-1,1,3-triphosphonic acid;
ethane-2-hydroxy-1,1,2-triphosphonic acid;

ethane-1-hydroxy-1,1,2-triphosphonic acid;
propane-1,3-diphenyl-2,2-diphosphonic acid;
nonane-1,1-diphosphonic acid;
hexadecane-1,1-diphosphonic acid;
pent-4-ene-1-hydroxy-1,1-diphosphonic acid;
octadec-9-ene-1-hydroxy-1,1-diphosphonic acid;
3-phenyl-1,1-diphosphonoprop-2-ene;
octane-1,1-diphosphonic acid;
dodecane-1,1-disphosphonic acid;
phenylaminomethanediphosphonic acid;
naphthylaminomethanediphosphonic acid;
N,N-dimethylaminomethanediphosphonic acid;
N-(2-hydroxyethyl)-aminomethanediphosphonic acid;
N-acetylaminomethanediphosphonic acid;
aminomethanediphosphonic acid;

and the pharmaceutically acceptable salts of these acids, e.g., sodium, potassium, calcium, magnesium ammonium, triethanolammonium, diethanolammonium and monoethanolammonium salts.

Mixtures of any of the foregoing phosphonic acids and/or salts can be used in the compositions of this invention.

Ethane-1-hydroxy-1,1-diphosphonic acid, an especially preferred polyphosphonate, has the molecular formula $CH_3C(OH)(PO_3H_2)_2$. (According to nomenclature by radicals, the acid might also be named 1-hydroxyethylidene diphosphonic acid.) The most readily crystallizable salt of this acid is obtained when three of the acid hydrogens are replaced by sodium. Preferred salts for the purpose of this invention are the trisodium hydrogen salt which has the structure:

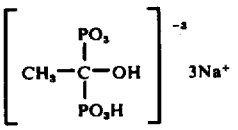

and the disodium salt.

The trisodium hydrogen salt normally crystallizes as the hexahydrate which loses some water during air-drying to yield a mixture of the hexa- and monohydrate averaging 3 to 4 molecules of water of hydration.

While any pharmaceutically acceptable salt of ethane-1-hydroxy-1,1-diphosphonic acid can be used in the practice of this invention, the tetrasodium salt, the trisodium hydrogen salt, the disodium dihydrogen salt, the monosodium trihydrogen salt, the monocalcium salt and the mixtures thereof preferred. The other pharmaceutically acceptable salts and mixtures thereof are also suitable. These compounds can be prepared by any suitable method, however, an especially preferred method is disclosed in copending application Ser. No. 553,648, fled May 31, 1966, by Oscar T. Quimby et al., now Patent No. 3,400,149.

Methanehydroxydiphosphonic acid and related compounds operable herein can be prepared, for example, by reaction of phosgene with an alkali metal dialkyl phosphite. A complete description of these compounds and the method for preparing same is found in copending patent application Ser. No. 517,073, filed Dec. 29, 1965, by Oscar T. Quimby, now Patent No. 3,422,137.

Methanediphosphonic acid and related compounds useful herein are described in detail in U.s. Patent 3,213,030, granted Oct. 19, 1965. A preferred method of preparing such compounds is disclosed in copending application Ser. No. 218,862, filed Aug. 23, 1962, by Clarence H. Roy, now Patent No. 3,251,907.

Ethane-1,1,2-triphosphonic acid and related compounds which can be used in the compositions of this invention as well as a method for their preparation are fully described in copending patent application Ser. No. 602,161, filed Dec. 16, 1966, by Oscar T. Quimby.

Propane-1,1,3,3-tetraphosphonic acid and related compounds useful herein, and a method for preparing same are fully disclosed in copending application Ser. No. 507,662, filed Nov. 15, 1965, by Oscar T. Quimby, now Patent No. 3,400,176.

Pentane-2,2-diphosphonic acid and related compounds can be prepared in accordance with the method described by G. M. Kosolopoff in J. Amer. Chem. Soc., 75, 1500 (1953).

Propane-1,2,3-triphosphonic acid and salts thereof can be prepared by a process disclosed in the commonly assigned copending application of D. Allan Nicholson and Darrel Campbell, Ser. No. 694,002, filed Dec. 27, 1967.

Butane-1,2,3,4-tetraphosphonic acid and salts thereof can be prepared by a process disclosed in the commonly assigned copending application of D. Allan Nicholson and Darrel Campbell, Ser. No. 694,003, filed Dec. 27, 1967.

The higher aliphatic vicinal polyphosphonates and salts thereof can be prepared by the process disclosed in the commonly assigned copending application of D. Allan Nicholson and Darrel Campbell, Ser. No. 693,898, filed Dec. 27, 1967.

The concentration of polyphosphonate in the oral compositions of this invention can range from about .01% to about 10% by weight. Oral compositions which in the ordinary course of usage could be accidentally ingested should contain lower concentrations of polyphosphonate. Thus, a mouthwash in accordance with this invention preferably contains less than about 3% by weight of polyphosphonate. Dentifrice compositions, topical solutions and prophylaxis pastes, the latter to be administered professionally, can contain up to about 10% by weight, preferably from about 0.1% to about 5.0% by weight of polyphosphonate.

The pH of the composition of this invention can range from about 5.0 to about 11. Below about pH 5.0 damage to the dental enamel can occur in spite of the relative safety of the polyphosphonates. Above about pH 11.0 difficulty is encountered in formulating products having satisfactory flavor and mildness. A preferred pH range is from about 7.0 to about 10. The pH of the composition, of course, is determinative of the predominant salt form of the polyphosphonates present therein. For example, at pH 7.0 ethane-1-hydroxy-1,1-diphosphonate is predominantly in the disodium form.

While it is not intended that this invention be limited by a particular theory of operation, it has been observed that the polyphosphonates encompassed herein interfere with the progress of calculus formation by interferring with the conversion of amorphous calcium phosphate to crystalline calcium hydroxylapatite. Amounts of polyphosphonates which are much too small to chelate any appreciable quantities of calcium have been found to retard the formation of calcium hydroxylapatite. This selective action on the formative calculus deposits without demineralizing action on the dental enamel is surprising.

The efficacy of the compositions of this invention in calculus prophylaxis was demonstrated by the Rat Calculus and Crystal Growth Inhibition Tests which were conducted as follows:

Rat calculus study (topical)

Two groups of 20- to 21-day-old Holtzman-Sprague-Dawley strain rats, each group comprising one male and one female member of each of 10 liters, were employed in this test, one group serving as the control and the other serving as the test group. Both groups of animals were placed on a calculus inducing diet consisting of 63% cornstarch, 32% non-fat dry milk, 2% liver powder and 3% celluflour. Topical applications of a 0.5% aqueous solution of trisodium hydrogen ethane-1-hydroxy-1,1-diphosphonate adjusted to pH 10.0 were made on the teeth of each of the animals in the test group for about one minute twice daily, five days per week for three weeks. Similar applications of water were made to each animal in the control group during the experimental period.

Three weeks after the commencement of the test, the animals were sacrificed and their molars were graded for severity of calculus by assessing the area and depth of accumulation on each of the 44 dental surfaces examined in each animal. Grading was made on a 0–3 scale for each surface, 0 being no detectable calcified deposits, 3 being coverage of 50–100% of the surface with a thick deposit and intermediate values representing gradations between these extremes. The total calculus score for each animal was determined by adding the grades for each of the 44 surfaces.

The results obtained in two such experiments are set forth in Table 1 below.

TABLE I

| | Average of Total Calculus Scores | | |
|---|---|---|---|
| Experiment No. | Test | Control | Percent reduction |
| 1 | 2.4 | 6.8 | 65 |
| 2 | 11.2 | 27.2 | 59 |

It can be seen that substantial reductions in calculus formation are attained with topically applied compositions in accordance with this invention.

Crystal growth inhibition determination

As hereinbefore stated, the polyphosphonates inhibit the growth of calcium hydroxylapatite crystals and in this way interfere with the normal formation of calcium hydroxylapatite from solution. This test is to determine the effect of the polyphosphonates on the calcium phosphate formed on addition of calcium ion to orthophosphate ion at constant pH. The procedure is as follows:

1 ml. of a 0.1 M stock solution of $NaH_2PO_4 \cdot H_2O$ is diluted with 22 ml. of distilled water. 1 ml. of an aqueous solution of the polyphosphonate to be tested (at a concentration sufficient to provide the desired ultimate concentration in the reaction mixture) is added to the diluted $NaH_2PO_4$ solution and the solution is adjusted to pH 7.4 with sodium hydroxide. To this solution is added 1 ml. of a 0.1 M solution of $CaCl_2 \cdot 2H_2O$ preadjusted to pH 7.4 with sodium hydroxide. This mixture is held at a constant pH 7.4 throughout the reaction period.

After a sufficient reaction time as determined by the operator, generally within 90 minutes, the solution is filtered through a 0.45$\mu$ Millipore filter pad. The precipitate is air-dried and analyzed by X-ray diffraction. The solid calcium phosphate precipitated from the above-described solution without a polyphosphonate gives a typical hydroxylapatite pattern, while the calcium phosphate precipitated under the same conditions but in the presence of small amounts of the polyphosphonates of this invention is amorphous to X-rays.

Those compounds which were effective in inhibiting the growth of hydroxylapatite crystals at concentrations of less than $1.5 \times 10^{-3}$ m. under the conditions of this test were found to be effective in reducing calculus formation in rats, while several compounds outside the scope of this invention that had little or no effect in this test did not reduce calculus in rats.

Table 3 below shows the concentration of various polyphosphonates tested required to inhibit the formation of calcium hydroxylapatite under the conditions specified above.

TABLE 3

| Compound | M Concentration for Inhibition |
|---|---|
| Ethane-1-hydroxy-1,1-diphosphonic acid, trisodium salt | $2.00\times10^{-4}$ |
| Methane diphosphonic acid, trisodium salt | $1.82\times10^{-4}$ |
| Methanehydroxydiphosphonic acid, disodium salt | $2.04\times10^{-4}$ |
| Ethane-1,1,2-triphosphonic acid, tetrasodium salt | $2.00\times10^{-4}$ |
| Propane-1,1,3,3-tetraphosphonic acid, hexasodium salt | $1.16\times10^{-3}$ |
| Ethane-1-amino-1,1-diphosphonic acid | $1.00\times10^{-4}$ |
| Methanedichlorodiphosphonic acid. trisodium salt | $2.00\times10^{-4}$ |
| Nonane-5,5-diphosphonic acid | $2.00\times10^{-4}$ |
| n-Pentane-1,1-diphosphonic acid | $2.00\times10^{-4}$ |
| Nonane-1,1-diphosphonic acid, disodium salt | $2.01\times10^{-4}$ |
| Methanedibromodiphosphonic acid | $5.04\times10^{-5}$ |
| Ethane-2-carboxy-1,1-diphosphonic acid, tetrasodium salt | $2.26\times10^{-4}$ |
| Propane-1-hydroxy-1,1,3-triphosphonic acid, pentasodium salt | $1.02\times10^{-4}$ |
| Ethane-1-hydroxy-1,1,2-triphosphonic acid, pentasodium salt | $1.13\times10^{-3}$ |
| Ethane-2-hydroxy-1,1,2-triphosphonic acid, pentasodium salt | $1.05\times10^{-3}$ |
| Methaneaminodiphosphonic acid | $2.00\times10^{-4}$ |
| Phenylaminomethanediphosphonic acid | $2.60\times10^{-5}$ |
| N,N-dimethylaminomethanediphosphonic acid | $5.00\times10^{-5}$ |
| N-(2-hydroxyethyl)aminomethanediphosphonic acid | $5.20\times10^{-5}$ |
| N-acetylaminomethanediphosphonic acid | $2.22\times10^{-4}$ |
| Propane-1,2,3-triphosphonic acid | $2.32\times10^{-4}$ |
| Butane-1,2,3,4-tetraphosphonic acid | $2.04\times10^{-4}$ |
| Hexane-1,2,3,4,5,6-hexaphosphonic acid | $2.22\times10^{-4}$ |
| 3-phenyl-1,1-diphosphonoprop-2-ene, disodium salt | $2.04\times10^{-4}$ |

The presence of the specified amounts of the polyphosphonates of Table 3 in the test solutions of the Crystal Growth Inhibition Test results in the precipitation of an amorphous calcium phosphate rather than crystalline calcium hydroxylapatite as occurs without polyphosponate and the total formation of calcium orthophosphate is greatly decreased. By way of comparison, ethylenediaminetetraacetic acid and nitrilotriacetic acid which have been suggested for use as anticalculus agents in the art fail to inhibit crystal growth at molar concentrations of $2.45 \times 10^{-3}$ and $2.54 \times 10^{-3}$, respectively. At higher concentrations, these prior art compounds prevent precipitation of calcium phosphate in this test because of their powerful calcium sequestering properties.

The safety of polyphosphonates for use in contact with dental surfaces is determined by the Continuous Immersion Test conducted as follows: Mature human teeth are immersed in aqueous solutions or dispersions of oral compositions containing polyphosphonate in accordance with this invention at pH 7.0 and pH 10. Every four hours the teeth are examined for decalcification. Under visible light, enamel decalcification can be detected by a loss of luster, white opaque spots or slight surface roughening. The teeth are examined macroscopically and microscopically at the end of seven days. If no decalcification is observed through this period, the compositions cause no damage to dental enamel, and are considered safe in this respect for use in the oral cavity.

The safety of polyphosphonates for use in contact with dental enamel can also be established by measuring the amount of phosphate released from a given area of dental enamel in the course of a standard exposure to an aqueous soluton of the polyphosphonate as fully described by Tucker et al. in U.S. Pat. No. 3,175,951, granted Mar. 30, 1965.

A dentifrice, especially toothpaste, containing a polyphosphonate is a preferred embodiment of this invention. Toothpaste compositions conventionally contain abrasive materials, sudsing agents, binders, humectants, flavoring and sweetening agents.

The abrasive materials and other adjuncts used in the practice of this invention are preferably not sources of much soluble calcium so that the crystal growth inhibiting capacity of polyphosphonate is not depleted to an extent that its anticalculus activity is impaired. Thus, conventional abrasives such as dicalcium orthophosphate and calcium carbonate are preferably not used. However, predominantly β-phase calcium pyrophosphate prepared in accordance with the teachings of Schweizer, U.s. Pat. No. 3,112,247, granted Nov. 26, 1963, which contains relatively little soluble calcium can be used. An especially preferred class of abrasives for use herein are the particulate thermosetting polymerized resins as described by Cooley et al. in U.S. Pat. No. 3,070,510, granted Dec. 25, 1962. Suitable resins include, for example, melamines, phenolics, ureas, melamine-ureas, melamine-formaldehydes, urea-formaldehydes, melamine-urea-formaldehydes, cross-linked epoxides, and cross-linked polyesters.

Other suitable abrasives include alumina and the in soluble non-calcium metaphosphates such as sodium metaphosphate. Mixtures of abrasives can also be used. In any case, the total amount of abrasive in the dentifrice embodiments of this invention can range from 0.5% to 95% by weight of the dentifrice. Preferably, toothpastes contain from 20% to 60% by weight of abrasive. Abrasive particle size preferably ranges from $2\mu$ to $20\mu$.

Suitable sudsing agents are those which are reasonably stable and form suds throughout a wide pH range, preferably non-soap anionic organic synthetic detergents. Examples of such agents are water-soluble salts of alkyl sulfate having from 10 to 18 carbon atoms in the alkyl radical, such as sodium lauryl sulfate; water-soluble salts of sulfonated monoglycerides of fatty acids having from 10 to 18 carbon atoms, such as sodium monoglyceride sulfonates; salts of $C_{10}$–$C_{18}$ fatty acid amides of taurine, such as sodium N-methyl-N-palmitoyl taurine; salts of $C_{10}$–$C_{18}$ fatty acid esters of isethionic acid; and substantially saturated aliphatic acyl amides of saturated monoaminocarboxylic acids having 2 to 6 carbon atoms and in which the acyl radical contains 12 to 16 carbon atoms, such as sodium N-lauroyl sarcoside. Mixtures of two or more sudsing agents can be used.

The sudsing agent can be present in the dentifrice compositions of this invention in an amount from 0.5% to 5% by weight of the total compositions.

In preparing toothpastes, it is necessary to add some thickening material to provide a desirable consistency. Preferred thickening agents are hydroxyethyl cellulose and water-soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. Thickening agents in an amount from 0.5% to 5.0% by weight of the total composition can be used.

It is also desirable to include some humectant material in a toothpaste to keep it from hardening. Suitable humectants include glycerine, sorbitol, and other edible polyhydric alcohols. The humectant can comprise up to about 36% by weight of the toothpaste composition.

Suitable flavoring agents include oil of wintergreen, oil of peppermint, oil of spearmint, oil of sassafras, and oil of clove. Sweetening agents which can be used include saccharin, dextrose, levulose and sodium cyclamate.

Several representative oral compositions illustrating this invention are set forth in the following examples.

Example I

A toothpaste of the following compositions was prepared by conventional methods:

| | Parts by weight |
|---|---|
| Water | 31.58 |
| Sorbitol | 6.25 |
| Saccharin | 0.12 |
| Calcium pyrophosphate[1] | 39.00 |
| Glycerine | 18.00 |
| Sodium alkyl (coconut) sulfate | 0.40 |
| Sodium coconut monoglyceride sulfonate | 0.75 |
| Sodium carboxymethyl cellulose | 1.15 |
| Magnesium aluminum silicates | 0.40 |

-continued

| | Parts by weight |
|---|---|
| Flavoring | 0.85 |
| Disodium salt of ethane - 1 - hydroxy - 1,1 - diphosphonic acid | 1.50 |
| pH 5.90. | |

[1]Prepared in accordance with U.S. Patent 3,112,247 granted Nov. 26,1963.

This composition effectively retards calculus formation on dental enamel and when tested in the Continuous Immersion Test described herein no decalcification was noted after seven days exposure.

Toothpaste compositions substantially identical to the composition of Example I are prepared with the trisodium salt of methanediphosphonic acid; the disodium salt of methane-hydroxydiphosphonic acid; ethane-1-amino-1,1-diphosphonic acid; trisodium salt of methanedichlorodiphosphonic acid; and propane-2,2-diphosphonic acid, respectively, rather than the disodium salt of ethane-1-hydroxy-1,1-diphosphonic acid, adjusting the pH to 5.9. These compositions substantially retard calculus formation and do not decalcify dental enamel.

Example II

A toothpaste was prepared which was substantially identical in composition to the toothpaste of Example I except that 3.0 parts rather than 1.5 parts of disodium dihydrogen ethane-1-hydroxy-1,1-disphosphonate and 30.08 parts rather than 31.58 parts of water was used. This composition was also found to be effective and caused no damage to dental enamel after seven days exposure.

The disodium dihydrogen salt of ethane-1-hydroxy-1,1-diphosphonic acid in the above composition can be replaced by ethane-1-hydroxy-1,1-diphosphonic acid, or any of the potassium, ammonium, or substituted ammonium salts thereof, adjusting the pH of the composition to 7.0, and substantially equivalent results are attained.

Example III

Yet another toothpaste was prepared having the following composition:

| | Parts by weight |
|---|---|
| Water | 39.58 |
| Sorbitol | 6.25 |
| Saccharin | .12 |
| Abrasive (precipitated urea/formaldehyde condensate) | 31.00 |
| Glycerine | 18.00 |
| Sodium alkyl (coconut) sulfate | .40 |
| Sodium coconut monoglyceride sulfonate | .75 |
| Sodium carboxymethyl cellulose | 1.15 |
| Magnesium aluminum silicate | .40 |
| Flavoring | .95 |
| Disodium salt of ethane - 1 - hydroxy-1,1-diphosphonic acid | 1.50 |
| pH 5.3. | |

When employed in the customary manner, this toothpaste retards the formation of dental calculus and no decalcification of dental enamel was observed after seven days' exposure.

Several additional toothpastes are prepared having essentially the same composition as the toothpaste of Example III, but using the tetrasodium salt of ethane-1,1,2-triphosphonic acid; the pentasodium salt of propane-1-hydroxy-1,1,3-triphosphonic acid; the pentasodium salt of ethane-1-hydroxy-1,1,2-triphosphonic acid; the pentasodium salt of ethane-2-hydroxy-1,1,2-triphosphonic acid; ethane-2-naphthyl-1,1-diphosphonic acid; propane-1,2,3-triphosphonic acid, butane-1,2,3,4-tetraphosphonic acid, and hexane-1,2,3,4,5,6-hexaphosphonic acid, respectively, rather than the disodium salt of ethane-1-hydroxy-1,1-diphosphonic acid. The pH of these compositions is adjusted to 7.0. These toothpaste formulations effectively retard calculus formation on dental enamel without decalcifying same.

Example IV

A toothpaste composition prepared with 3.0 parts of disodium dihydrogen ethane-1-hydroxy-1,1-diphosphonate and 38.08 parts water, but otherwise substantially identical to the composition of Example III, was prepared. This composition was found to be effective against calculus formation and caused no observable decalcification of dental enamel after seven days' exposure.

The disodium dihydrogen salt of ethane-1-hydroxy-1,1-diphosphonic acid employed in this example can be replaced with dipotassium dihydrogen ethane-1-hydroxy-1,1-diphosphonate; diammonium dihydrogen ethane-1-hydroxy-1,1-diphosphonate; or bis(triethanolammonium)dihydrogen ethane-1-hydroxy-1,1-diphosphonate, respectively, adjusting the pH of the composition to 8.0. Substantially equivalent results are obtained with these compositions.

Several mouthwash compositions were prepared in accordance with this invention as follows:

| Example | V | VI | VII | VII |
|---|---|---|---|---|
| Component, parts by weight: | | | | |
| Glycerine | 10.0 | 10.0 | 10.0 | 10.0 |
| Ethyl alcohol | 16.5 | 16.5 | 16.5 | 16.5 |
| Water | 67.172 | 67.172 | 67.172 | 70.192 |
| Tween 80[1] | .12 | .12 | .12 | .12 |
| Saccharin | .045 | .045 | .045 | .02 |
| Sodium cyclamate | .075 | 0.75 | 0.75 | .04 |
| Flavor | .088 | .088 | .088 | .088 |
| EHDP[2] | 3.0 | 3.0 | 3.0 | 1.0 |
| pH[3] | 7.0 | 8.3 | 10.0 | 10.0 |

[1] Polyoxyethylene 120-moles of ethylene oxide sorbitan monooleate-a nomqnic emulsifier supplied by Atlas Powder Company

[2] Disodium salt of ethane-1-hydroxy-1,1-diphosphonic acid.

[3] Adjusted to value indicated with sodium hydroxide.

When used in the same manner as conventional mouthwash, at least once daily, each of the above compositions materially reduces accumulation of calculus on the surfaces of teeth. No decalcification was observed after seven days exposure of dental enamel to these compositions.

Mouthwash compositions corresponding to Example VII are prepared, substituting the dimagnesium salt of propane-1,1,3,3-tetraphosphonic acid; the disodium salt of propane-2,2-diphosphonic acid; the tetraammonium salt of ethane-2-carboxy-1,1-diphosphonic acid; nonane-5,5-diphosphonic acid; n-pentane-1,1-diphosphonic acid and ethane-2-phenyl-1,1-diphosphonic acid, respectively, for the disodium salt of ethane-1-hydroxy-1,1-diphosphonic acid and adjusting the pH to 10.0. These mouthwash compositions retard calculus formation without damaging tooth structure.

Mouthwash compositions corresponding to Example V are prepared, replacing the disodium salt of ethane-1-hydroxy-1,1-diphosphonic acid with pent-4-ene-1-hydroxy-1,1-diphosphonic acid; octadec-9-ene-1-hydroxy-1,1-diphosphonic acid; methane-dichlorodiphosphonic acid; methanedibromodiphosphonic acid; phenylaminoethanediphosphonic, respectively. Each of the resulting mouthwash compositions retard calculus formation without damaging dental enamel.

A number of additional mouthwash compositions are prepared which are similar in formulation to the composition of Example VIII but replacing the disodium salt of ethane-1-hydroxy-1,1-diphosphonic acid with the disodium salt of hexane-1-hydroxy-2,3,4,5,6-pentaphosphonic acid, the triammonium salt of hexane-1,6-dihydroxy-2,3,4,5-tetraphosphonic acid, the dicalcium salt of pentane-1,2,3,4,5-pentaphosphonic acid, heptane-1,2,3,4,5,6,7-heptaphosphonic acid and octane-1,2,3,4,5,6,7,8-octaphosphonic acid, respectively. These compositions are effective in retarding dental calculus formation without damaging dental enamel.

Example IX

A prophylaxis paste for use by the dentist for removal of stains and polishing the teeth after mechanical removal of calculus deposits is formulated as follows:

| | Parts by weight |
|---|---|
| Navajo pumice | 77.10 |
| $TiO_2$ | 4.00 |
| Glycerine | 17.75 |
| Hydroxyethylcellulose | .22 |
| Saccharin | .33 |
| Trisodium salt of ethane-1-hydroxy-1,1-diphosphonic acid | 8.0 |
| pH 8.0 | |

When applied to the teeth with a prophylactic rubber cup in the conventional manner, this composition retards the development of new calculus deposits.

The prophylaxis paste set forth above is modified by replacing the trisodium salt of ethane-1-hydroxydiphosphonic acid with N,N-dimethylaminoethanediphosphonic acid; N-(2-hydroxyethyl)aminomethanediphosphonic acid; N-acetylaminomethanediphosphonic acid; and aminomethanediphosphonic acid, respectively, with comparable results.

Moreover, dodecane-1,1-diphosphonic acid, the dipotassium salt of 3-phenyl-1,1-diphosphonoprop-2-ene, or the dimagnesium salt of decane-1,2,3,4,5,6,7,8,9,10-decaphosphonic acid can be used in place of the trisodium salt of ethane-1-hydroxy-1,1-diphosphonic acid in the composition of Example IX with good results.

Toothpowders and the like can be prepared by conventional methods and containing, in addition to the usual ingredients, an amount of polyphosphonate within the ranges specified herein, to provide an effective means of retarding calculus formation without damaging the tooth structure.

Those components other than polyphosphonates which were included in the foregoing examples and various mixtures of those components are illustrative of carriers suitable for use in the oral cavity.

In the reference to pH adjustments in the foregoing examples, it is to be understood that a base of a cation corresponding to the salt form of the polyphosphonate employed is used to adjust to higher pH values. In each case in which the polyphosphonate was added in its acid form to the example compositions, the pH was adjusted to the specified higher value with NaOH. Adjustments in pH to more acid levels is accomplished with HCl acid. It will be obvious to those skilled in the art that pH adjustments can be made with any acid or base suitable for use in the oral cavity.

What is claimed is:

1. [ An oral ] *A dentifrice* composition effective in inhibiting the formation of dental calculus without adversely affecting tooth structure, comprising (1) from about .01% to about 10% by weight of a polyphosphonate selected from the group consisting of those of the formulae:

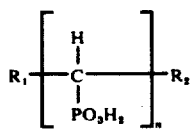

(I)

or

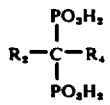

(II)

wherein $R_1$ and $R_2$ are each hydrogen or $CH_2OH$; n is an integer of from 3 to 10; $R_3$ is hydrogen, alkyl containing from 1 to about 20 carbon atoms, alkenyl containing from 2 to about 20 carbon atoms, phenyl, naphthyl, phenylethyl, benzyl, halogen, amino, dimethylamino, diethylamino, N-hydroxy-N-ethylamino, acetylamino, $-CH_2COOH$ $-CH_2PO_3H_2$, $-CH(PO_3H_2)(OH)$ or $-CH_2CH(PO_3H_2)_2$ $R_4$ is hydrogen, lower alkyl, amino, benzyl, halogen, hydroxyl $-CH_2COOH$, $CH_2PO_3H_2$, or $-CH_2CH_2PO_3H_2$; or a pharmaceutically acceptable salt thereof, and (2) [ a carrier suitable for use in the oral cavity, ] *from about 0.5% to 95% by weight of an abrasive material*, the pH of the compositon being within the range from about 5.0 to 11.0, *said composition being free of calcium abrasives which would yield enough soluble calcium to significantly impair the anticalculus activity of said polyphosphonate.*

2. The composition of claim 1 in which the polyphosphonate is ethane-1-hydroxy-1,1-diphosphonic acid or a pharmaceutically acceptable salt thereof.

3. The composition of claim 1 in which the polyphosphonate is methanediphosphonic acid or a pharmaceutically acceptable salt thereof.

4. The composition of claim 1 in which the polyphosphonate is methanedichlorodiphosphonic acid or a pharmaceutically acceptable salt thereof.

5. The composition of claim 1 in which the polyphosphonate is ethane-1-hydroxy-1,1,2-triphosphonic acid or a pharmaceutically acceptable salt thereof.

6. The composition of claim 1 in which the polyphosphonate is methanehydroxydiphosphonic acid or a pharamaceutically acceptable salt thereof.

7. The composition of claim 1 in which the polyphosphonate is propane-1,1,3,3-tetraphosphonic acid or a pharmaceutically acceptable salt thereof.

8. The composition of claim 1 in which the polyphosphonate is ethane-2-carboxy-1,1-diphosphonic acid or a pharmaceutically acceptable salt thereof.

9. The composition of claim 1 in which the polyphosphonate is ethane-1,1,2-triphosphonic acid or a pharmaceutically acceptable salt thereof.

10. The composition of claim 1 in which the polyphosphonate is ethane-1-amino-1,1-diphosphonic acid or a pharmaceutically acceptable salt thereof.

11. The composition of claim 1 in which the polyphosphonate is ethanedichlorodiphosphonic acid or a pharmaceutically acceptable salt thereof.

12. The composition of claim 1 in which the polyphosphonate is nonane-5,5-diphosphonic acid or a pharmaceutically acceptable salt thereof.

13. The composition of claim 1 in which the polyphosphonate is n-pentane-1,1-diphosphonic acid or a pharmaceutically acceptable salt thereof.

14. The composition of claim 1 in which the polyphosphonate is methanedibromodiphosphonic acid or a pharmaceutically acceptable salt thereof.

15. The composition of claim 1 in which the polyphosphonate is propane-1-hydroxy-1,1,3-triphosphonic acid or a pharmaceutically acceptable salt thereof.

16. The composition of claim 1 in which the polyphosphonate is propane-1,2,3-triphosphonic acid or a pharmaceutically acceptable salt thereof.

17. The composition of claim 1 in which the polyphosphonate is butane-1,2,3,4-tetraphosphonic acid or a pharmaceutically acceptable salt thereof.

18. The composition of claim 1 in which the polyphosphonate is hexane-1,2,3,4,5,6-hexaphosphonic acid or a pharmaceutically acceptable salt thereof.

19. A toothpaste composition comprising (1) from about 0.1% to about 5.0% by weight of a polyphosphonate selected from the group consisting of those of the formulae:

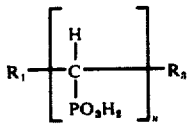

(I)

or

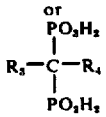

(II)

wherein $R_1$ and $R_2$ are each hydrogen or $CH_2OH$; n is an integer of from 3 to 10; $R_3$ is hydrogen, alkyl containing from 1 to about 20 carbon atoms, alkenyl containing from 2 to about 20 carbon atoms, phenyl, naphthyl, phenylethenyl, benzyl, halogen, amino, dimethylamino, diethylamino, N-hydroxy-N-ethylamino, acetylamino, $—CH_2COOH$ $—CH_2PO_3H_2$, $—CH(PO_3H_2)(OH)$ or $—CH_2CH(PO_3H_2)_2$ $R_4$ is hydrogen, lower alkyl, amino, benzyl, halogen, hydroxyl, $—CH_2COOH$, $—CH_2PO_3H_2$, or $—CH_2CH_2PO_3H_2$; or a pharmaceutically acceptable salt thereof, and (2) from about 20% to about 60% by weight of an abrasive material, the pH of said composition being within the range from about 7 to about 10, *said composition being free of calcium abrasives which would yield enough soluble calcium to significantly impair the anticalculus activity of said polyphosphonate.*

20. The composition of claim 19 in which the polyphosphonate is ethane-1-hydroxy-1,1-diphosphonic acid or a pharmaceutically acceptable salt thereof.

*21. The composition of claim 19 wherein the abrasive material is selected from the group consisting of β-phase calcium pyrophosphate, thermosetting polymerized resins, alumina and insoluble non-calcium metaphosphates.*

* * * * *